(12) United States Patent
Mansuripur

(10) Patent No.: US 12,364,619 B2
(45) Date of Patent: *Jul. 22, 2025

(54) SURGICAL JIG AND METHOD FOR USING SAME

(71) Applicant: Traktus LLC, Berkeley, CA (US)

(72) Inventor: Peter Kaveh Mansuripur, Berkeley, CA (US)

(73) Assignee: TRAKTUS LLC, Berkeley, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 18/451,609

(22) Filed: Aug. 17, 2023

(65) Prior Publication Data

US 2024/0065873 A1   Feb. 29, 2024

Related U.S. Application Data

(62) Division of application No. 17/821,588, filed on Aug. 23, 2022, now Pat. No. 11,771,581.

(51) Int. Cl.
*A61F 5/048*      (2006.01)
*A61F 5/058*      (2006.01)

(52) U.S. Cl.
CPC .......... *A61F 5/048* (2013.01); *A61F 5/05875* (2013.01)

(58) Field of Classification Search
CPC ...... A61F 5/048; A61F 5/05875; A61F 5/042; A61F 5/04; A61F 5/05866; A61F 5/10; A61F 2007/0037; A61F 13/104; A61F 13/105; A61F 2/42; A61F 2/4241
See application file for complete search history.

(56) References Cited

U.S. PATENT DOCUMENTS 7,131,955 B2 *  11/2006  Price ..................... A61F 5/3761
                                                                602/20
11,771,581 B1 * 10/2023  Mansuripur ............ A61F 5/048
                                                                602/22

* cited by examiner

*Primary Examiner* — Tarla R Patel
(74) *Attorney, Agent, or Firm* — Husch Blackwell LLP; Bryan D. Stewart; Andrew C. Landsman

(57) ABSTRACT

Provided herein is a surgical jig and methods for making and using the same. In at least one embodiment, the jig contains a forearm strap and finger strap to secure a patient's forearm and hand, respectively, to the jig, and at least one finger attachment site configured to receive and secure a fractured finger to the jig. The jig is designed to position the hand and finger in an optimal position for fracture reduction by a clinician while utilizing minimal resources. In various embodiments, the present methods of using the jig include adjustment of the patient's hand by the clinician to ensure optimal placement of the fractured finger prior to commencing fracture reduction.

13 Claims, 9 Drawing Sheets

SURGICAL JIG AND METHOD FOR USING SAME

CROSS-REFERENCE TO RELATED APPLICATIONS

This application is a divisional of and claims the benefit of priority to U.S. patent application Ser. No. 17/821,588, filed on Aug. 23, 2022, the contents of which are hereby incorporated by reference.

FIELD OF THE DISCLOSURE

The present disclosure relates to surgical jigs. In particular, this disclosure relates to surgical jigs for fracture reduction procedures of the small bones of a hand.

BACKGROUND

The hand has 27 total bones (not including the sesamoid bones): fourteen phalanges, five metacarpals, and eight carpal bones. The eight carpal bones are organized into a proximal row which articulates with the bones of the forearm, and a distal row, which articulates with the bases of the five metacarpal bones of the hand. The heads of the metacarpals each in turn articulate with the bases of the proximal phalanx of the fingers and thumb to form the metacarpophalangeal (MCP) joints, also referred to as knuckles. The fourteen phalanges make up the fingers and thumb, the four fingers each consist of three phalanx bones: proximal, middle, and distal. The thumb only consists of a proximal and distal phalanx. The distal interphalangeal (DIP) joints are located at the tip of the finger, just before the fingernails start. The proximal interphalangeal (PIP) joints are located between the proximal and middle phalanxes. The carpometacarpal (CMC) joints articulate between the carpals and metacarpals. Together with the phalanges these metacarpal bones form five rays or poly-articulated chains. "Finger," as used herein for the purposes of this disclosure, comprises all digits of a hand, including the thumb.

Bones, such as bones of a hand, may be anatomically misaligned or fractured where fracture reduction procedures are needed to realign the bones and alleviate pain felt by the affected patient. There is inherent complexity involved with manual realignment of bones due to imprecision concerns and costly use of resources such as the efforts of multiple medical professionals just to hold a fractured finger in a desired position, which can lead to inconsistent treatment results. Such corrective fracture reduction procedures include, but are not limited to, surgeries. As a result, there is a need for a jig that can be used in fracture reduction surgeries that can reliably and consistently hold a patient's fractured finger in a desired position, while also freeing up operating room resources to perform other functions.

SUMMARY

According to a first aspect, the present disclosure relates to a jig including: (i) a base having a first end and a second end; (ii) a first support positioned at the first end; (iii) a second support positioned between the first end and the second end; (iv) a finger attachment attached to the first support via a plurality of elongate members; (v) a finger strap positioned between the second support and the first end, the finger strap selectively wrapping around the second support; and (vi) a forearm strap positioned between the second support and the second end, the forearm strap selectively wrapping around the base. In alternative embodiments, the jig may not include each feature (i)-(vi), but rather may only include some of the aforementioned features.

According to a second aspect, the jig of the first aspect or any other aspect, wherein the second support is attached to the base.

According to a third aspect, the jig of the second aspect or any other aspect, wherein the position of the second support is adjustable in relation to the first end and the second end.

According to a fourth aspect, the jig of the first aspect or any other aspect, wherein the plurality of elongate members comprise a plurality of chains.

According to a fifth aspect, the jig of the first aspect or any other aspect, wherein the plurality of elongate members comprise a plurality of wires.

According to a sixth aspect, the jig of the first aspect or any other aspect, wherein the plurality of elongate members comprise a plurality of straps.

According to a seventh aspect, the jig of the first aspect or any other aspect, wherein the plurality of elongate members comprise a first elongate member and a second elongate member.

According to an eighth aspect, the jig of the seventh first aspect or any other aspect, wherein the finger attachment selectively receives a finger; and the first elongate member and the second elongate member are attached to the finger attachment in a coronal plane of the finger when the finger is received in the finger attachment.

According to a ninth aspect, the jig of the eighth aspect or any other aspect, wherein the finger attachment, the first elongate member, and the second elongate member enable positioning of the finger in the coronal plane.

According to a tenth aspect, the jig of the ninth aspect or any other aspect, wherein the finger attachment, the first elongate member, and the second elongate member provide rotational control of the finger.

According to an eleventh aspect, the jig of the tenth aspect or any other aspect, wherein changing the position of the first elongate member or the second elongate member adjusts the orientation of the finger attachment in relation to the second support.

According to a twelfth aspect, the jig of the first aspect or any other aspect, further comprising at least one guide tower positioned between the first support and the second support.

According to a thirteenth aspect, the jig of the twelfth aspect or any other aspect, wherein the guide tower comprises a k-wire guide.

According to a first aspect of a method for reducing a fracture of a patient's finger, using the fracture reduction jig described above, the method includes the steps of: (i) inserting the patient's forearm through the forearm strap; (ii) positioning the patient's hand in contact with the second support; (iii) inserting the patient's fractured finger into the finger attachment; (iv) applying traction to the fractured finger; (v) securing the patient's remaining fingers to the second support using the finger strap; (vi) securing the patient's forearm to the fracture reduction jig using the forearm strap; (vii) adjusting the finger attachment to align the fractured finger; (viii) checking fracture reduction and overall alignment; and (ix) performing a definitive fixation of the fracture.

According to a second aspect, the method of the first aspect or any other aspect, wherein the plurality of elongate members comprise chains attached to the finger attachment at a first end and wherein the chains are removably attached to the first support.

According to a third aspect, the method of the first aspect or any other aspect, wherein the step of adjusting the finger attachment to align the fracture is performed by adjusting the attachment of the elongate members to the first support.

According to a fourth aspect, the method of the first aspect or any other aspect, wherein further including the step of applying percutaneous reduction clamps to reduce the fracture.

According to a fifth aspect, the method of the first aspect or any other aspect, further including the step of positioning the fractured finger in an optimal position for antegrade k-wire fixation.

According to a sixth aspect, the method of the first aspect or any other aspect, wherein the definitive fixation is performed using a k-wire fixation technique.

According to a seventh aspect, the method of the first aspect or any other aspect, wherein the definitive fixation is performed using percutaneous screw placement.

According to a first aspect of a second method of using the fracture reduction jig described above, the method includes the steps of: (i) positioning the patient's hand in contact with the second support; (ii) inserting the patient's fractured finger into the finger attachment; (iii) applying traction to the fractured finger; (iv) securing the patient's remaining fingers to the second support using the finger strap; (v) securing the patient's forearm to the fracture reduction jig using the forearm strap; (vi) adjusting the finger attachment to align the fractured finger; (vii) checking fracture reduction and overall alignment; and (viii) performing a definitive fixation of the fracture.

According to a second aspect, the second method of the first aspect or any other aspect, further including the step of applying percutaneous reduction clamps to reduce the fracture.

According to a third aspect, the second method of the first aspect or any other aspect, further including the step of positioning the fractured finger in an optimal position for antegrade k-wire fixation.

According to a fourth aspect, the second method of the first aspect or any other aspect, wherein the definitive fixation is performed using a k-wire fixation technique.

According to a fifth aspect, the second method of the first aspect or any other aspect, wherein the definitive fixation is performed using a percutaneous screw placement technique.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from the principles of this disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

DETAILED DESCRIPTION

Figure 1:
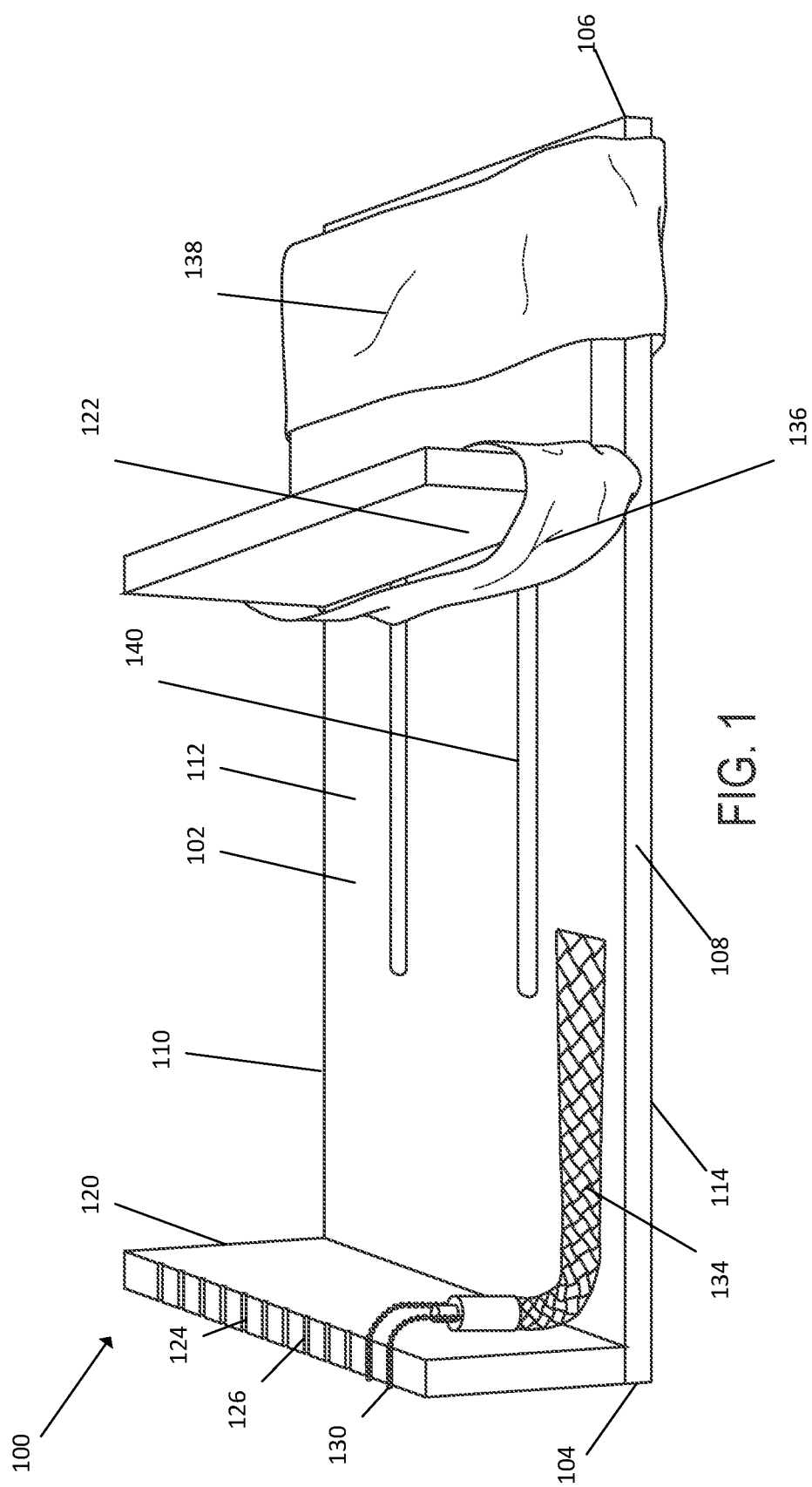
FIG. 1 is a perspective view of one embodiment of a finger fracture reduction jig according to the principles of this disclosure.
Figure 2:
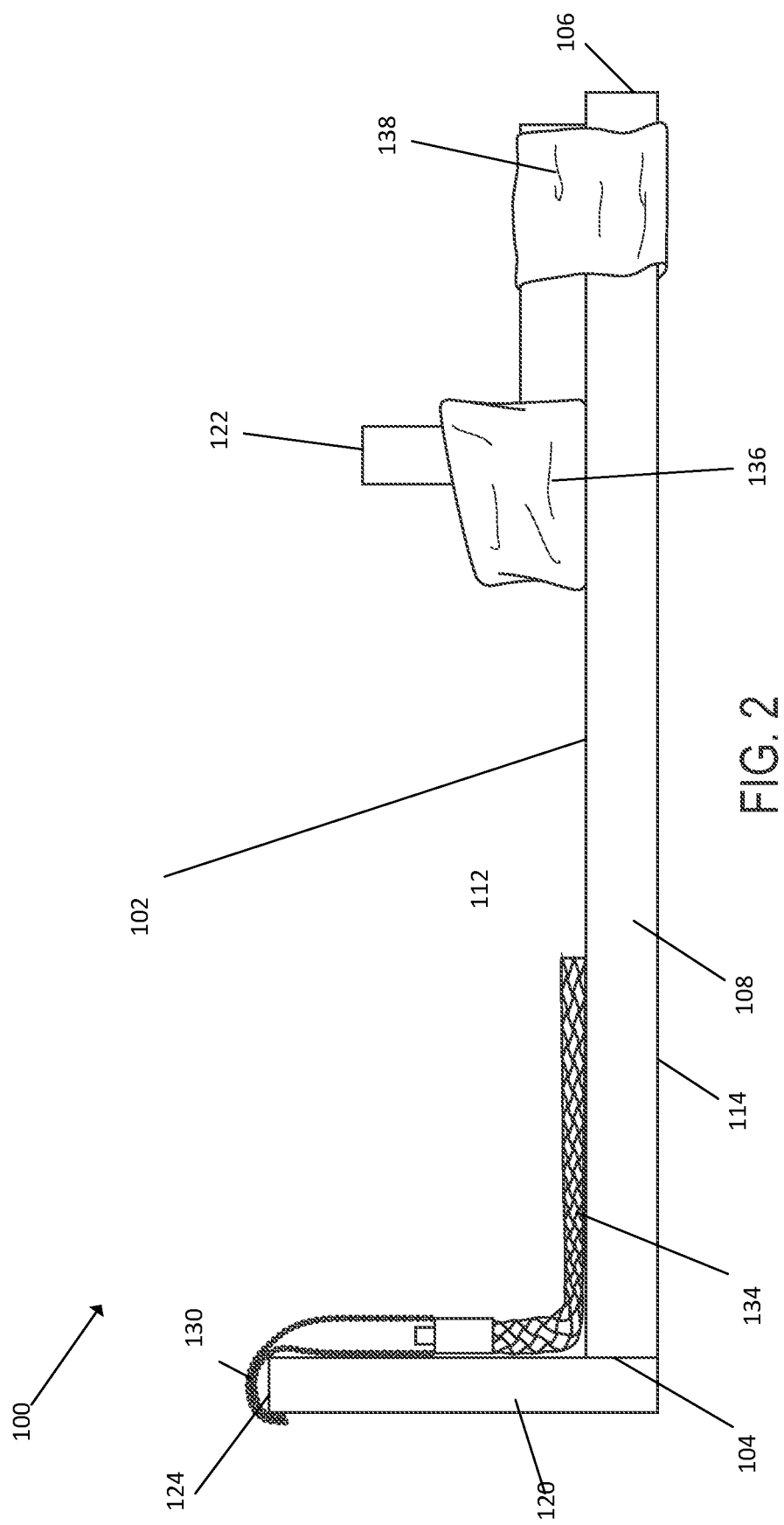
FIG. 2 is a side view of the jig of FIG. 1.
Figure 3:
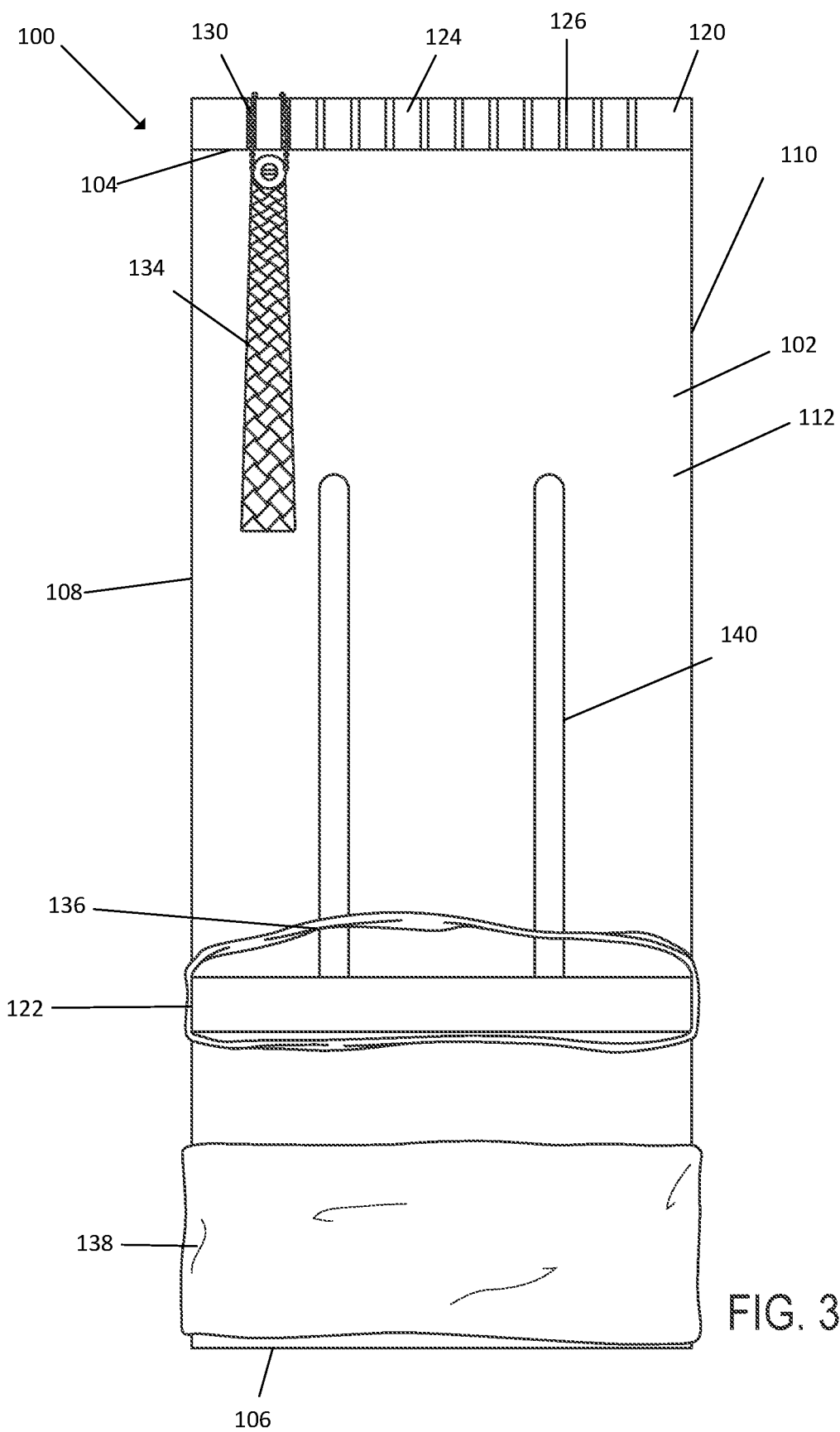
FIG. 3 is a top view of the jig of FIG. 1.

Referring now FIGS. 1-3, one embodiment of a finger fracture reduction jig 100 according to the principles of this disclosure is shown. Jig 100 includes a base 102 having a first end 104, a second end 106, a first side 108, a second side 110, a top surface 112, and a bottom surface 114. In the embodiment shown, base 102 has a generally rectangular shape, although alternative shapes may be used without departing from the principles of this disclosure. In certain embodiments, base 102 may comprise a plurality of separate components—two or more rails, for example—that may be secured at first end 104 and second end 106.

In various embodiments, a first support 120 is attached to base 102 at first end 104 and extends substantially vertically from top surface 112. In certain embodiments, first support 120 may be integrally formed with base 102. In the embodiment shown, first support 120 includes a plurality of notches 126 distributed along a top edge 124. In certain embodiments, notches 126 are distributed uniformly along top edge 124. In certain alternative embodiments, notches 126 are positioned in any desired distribution without departing from the principles of this disclosure.

A second support 122 may be attached to base 102 between first end 104 and second end 106 and also extends substantially vertically from top surface 112. In certain embodiments, the position of second support 122 is adjustable in relation to first end 104 and second end 106. In some embodiments, second support 122 may be integrally formed with base 102. As will be further discussed herein, in some embodiments, a finger strap 136 is wrapped around second support 122 and a forearm strap 138 is wrapped around base 102 between second support 122 and second end 106.

In certain embodiments, base 102 includes a plurality of slots 140 that extend between first support 120 and second support 122. In such embodiments, the position of second support 122 may be adjustable along slots 140 in relation to first end 104 and second end 106. Adjusting the position of second support 122 changes the distance between first support 120 and second support 122, and second support 122 and second end 106 of jig 100. Such adjustment may allow jig 100 to be used on patients with a range of hand sizes.

In certain alternative embodiments, base 102 may include a single slot 140 or more than two slots without departing from the principles of this disclosure. In such embodiments, slot 140 may have a variety of suitable widths. Second support 122 may be secured to base 102 in a variety of ways including, but not limited to, latches, fasteners, straps, hook and loop, and 3M® Dual Lock® reclosable fasteners. In certain embodiments, a plurality of holes or other suitable components for adjusting the position of second support 122 may be used without departing from the principles of this disclosure. In certain alternative embodiments, strips of one side of hook and loop or Dual Lock® fasteners may be adhered to base 102, with an opposite side of the hook and loop or Dual Lock® adhered to second support 122, which would allow the second support to be removed and repositioned in a variety of suitable positions without the use of tools.

During a fracture reduction procedure, the clinician may find it helpful to use x-rays when positioning the patient's hand in an optimal position, and radiolucent materials will not appear under x-ray imaging. Radiolucent materials are generally composites such as fiber reinforced thermoplastic resins. These composites have physical properties that make them suitable for use in surgical procedures. Some examples of thermoplastic resins used in the manufacturing of medical-application composites include, but are not limited to, polyamides (nylons), polyetherimides, polyphenylenes, and polyaryletherketones. Some examples of fiber reinforcements used in the manufacturing of medical-application composites include, but are not limited to, chopped fibers of random orientation or continuous fibers of unidirectionality or bidirectionality. Some common manufacturing methods used for radiolucent structural components include, but are not limited to compression molding, injection molding, and extrusion.

In certain embodiments, one or more of base 102, first support 120, second support 122 are made of radiolucent material that may also be capable of being sterilized and reused. In certain alternative embodiments, the radiolucent materials may be disposable. It may be desirable that jig 100 is at least partially radiolucent so that it is transparent under x-rays and other types of radiation.

Non-radiolucent materials or other suitable materials may alternatively be used for certain components without departing from the principles of this disclosure. For example, base 102 may include one or more cutouts between first support 120 and second support 122. Such cutouts may be in addition to slots 140 or in lieu of the same. Including cutouts rather than slots 140, may allow base 102 to be made of non-radiolucent material, while still allowing the finger 204 to be visible under x-ray. Of course, some or all of the base 102, first support 120, and second support 122 may be made of any of the aforementioned materials, in any suitable combination.

Further, base 102 may include a variety of other features. For example, in various embodiments, base 102 may include one or more holes for placing additional components or mechanisms. Continuing with this example, the base 102 includes a variety of holes that allows a surgeon to place a carbon-fiber rod (on either side of a patient's finger) to provide a fulcrum for bending the patient's finger around the carbon-fiber rod. Continuing with the same example, a surgeon uses the variety of holes in the base 102 to place other equipment (e.g., a guide tower discussed herein) for positioning a patient's fingers (including a patient's thumb) or providing other benefits.

As shown in FIGS. 1 and 3, a plurality of notches 126 are included along top edge 124 of first support 120. The notches 126 may allow for selective positioning of elongate members 130 to first support 120. The plurality of elongate members 130 may be adjustable over any suitable combination of notches 126. As will be understood, in various embodiments, adjusting the position of elongate members 130 adjusts the position of finger attachment 134.

In the embodiment shown, two elongate members 130 are attached to finger attachment 134. Elongate members 130 may be made of stainless steel or other suitable materials. In addition, elongate members 130 may be in the form of chains (ball chain type or other type of chain), wires, or straps that may be made of radiolucent, non-radiolucent, or any other suitable material or any other form without departing from the principles of this disclosure. In the embodiment shown, elongate members 130 may selectively engage notches 126 by friction, which may temporarily secure each elongate member to a slot. In certain alternative embodiments, notches 126 may merely guide elongate members 130 over first support 120. In such embodiments, elongate members 130 may be secured to first support 120, base 102, or other location by a clasp, hook, or other suitable fastener.

Figure 7:
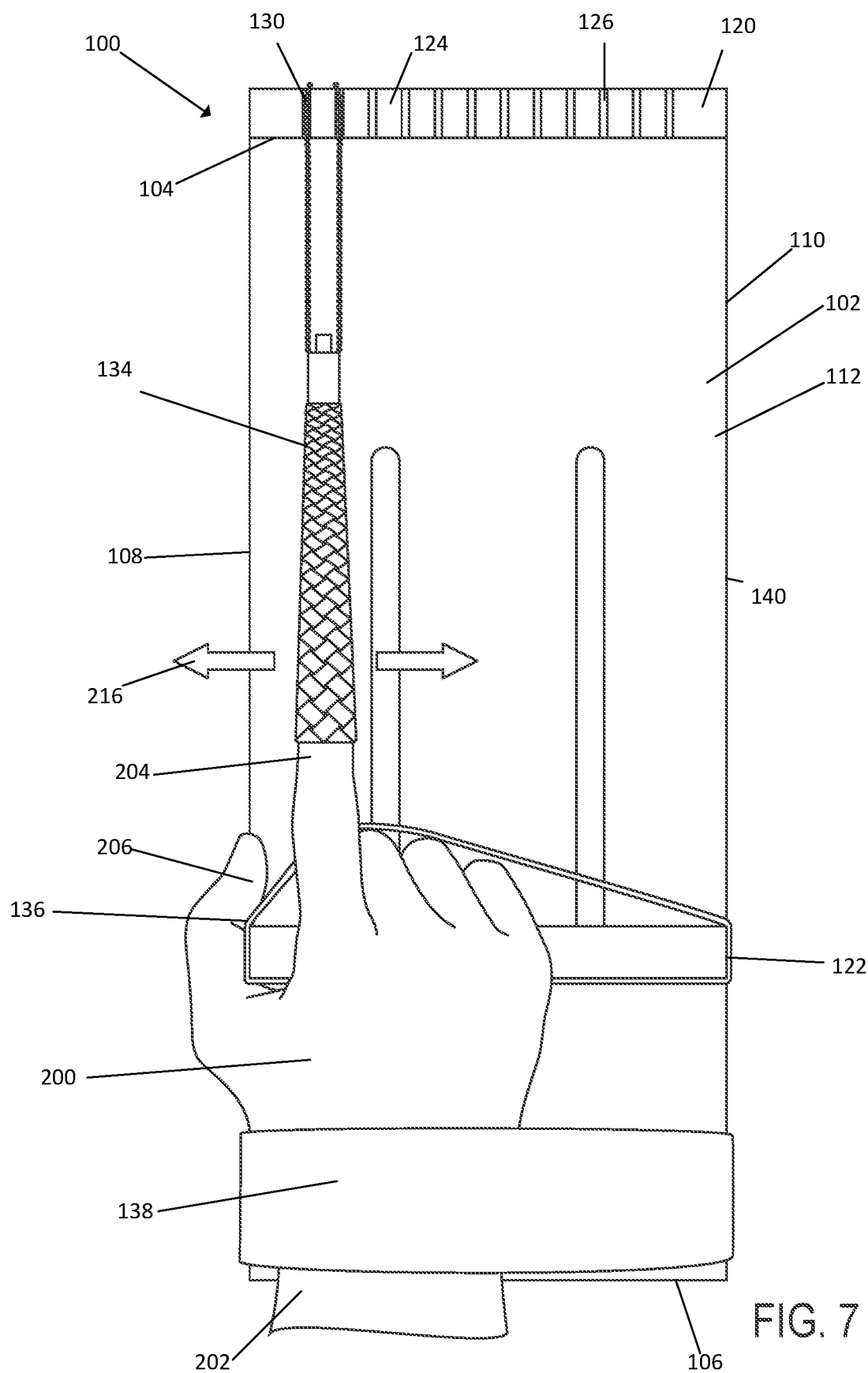
FIG. 7 is another top view of the jig of FIG. 1, showing a patient's hand and forearm secured to the jig.

In certain embodiments, a guide tower in the form of a k-wire guide is optionally included in the jig system. In general, k-wires are stiff, straight wires that are used to repair a fracture by keeping bones in place in place until they heal. As used herein, "k-wire" may include any suitable wire, rod, or rod-like instrument/device, including a guide wire or other device. The guide tower assists in the accurate placement and removal of k-wires which, in turn, promotes healing. The guide tower may include a generally flat component that provides stability for placing a k-wire (or similar instrument/device) and may include a mechanism for making micro or other adjustments to the k-wire location. For example, the guide tower may include a plurality of holes which receive a k-wire. In this example, the guide tower may include millimeter or less spacing between the holes, allowing a surgeon to place a first k-wire in a first hole, then micro-adjust placement by placing a second k-wire through a second hole in the guide tower. As will be understood from discussions herein, a guide tower may be located on either side of a patient's finger (e.g., patient's finger as shown in FIG. 7).

Finger attachment 134 may be made of a plurality of fibers woven into generally cylindrical, conical, or any other suitable shape. Examples include Chinese finger traps, "towing socks," "pulling grips," straps, or any other suitable alternatives. In certain embodiments, finger attachment 134 may be made of radiolucent material that is also capable of being sterilized and reused. Example materials include but are not limited to thermoplastic fabric or webbings such as nylon, polypropylene, Kevlar, polyetheretherketone (PEEK), polyphenylene sulfide (PPS), metallic materials, and others. In certain embodiments, finger attachment 134 may be made of non-radiolucent material—stainless steel, for example—or any other suitable material without departing from the principles of this disclosure. In certain embodiments, finger attachment 134 may comprise a finger sleeve that may be elastic, neoprene, or other suitable material. Such finger sleeves may also be shaped in a way that provides suitable attachment to the fractured finger during the reduction procedure. In certain other embodiments, finger attachment 134 may comprise either or both of finger strap 136 and forearm strap 138 may also be made of radiolucent material that is also capable of being sterilized and reused. Example materials include but are not limited to thermoplastic fabric such as Kevlar, PEEK, or PPS. In certain embodiments, finger strap 136 may be made of non-radiolucent material or any other suitable material without departing from the principles of this disclosure.

Figure 4:
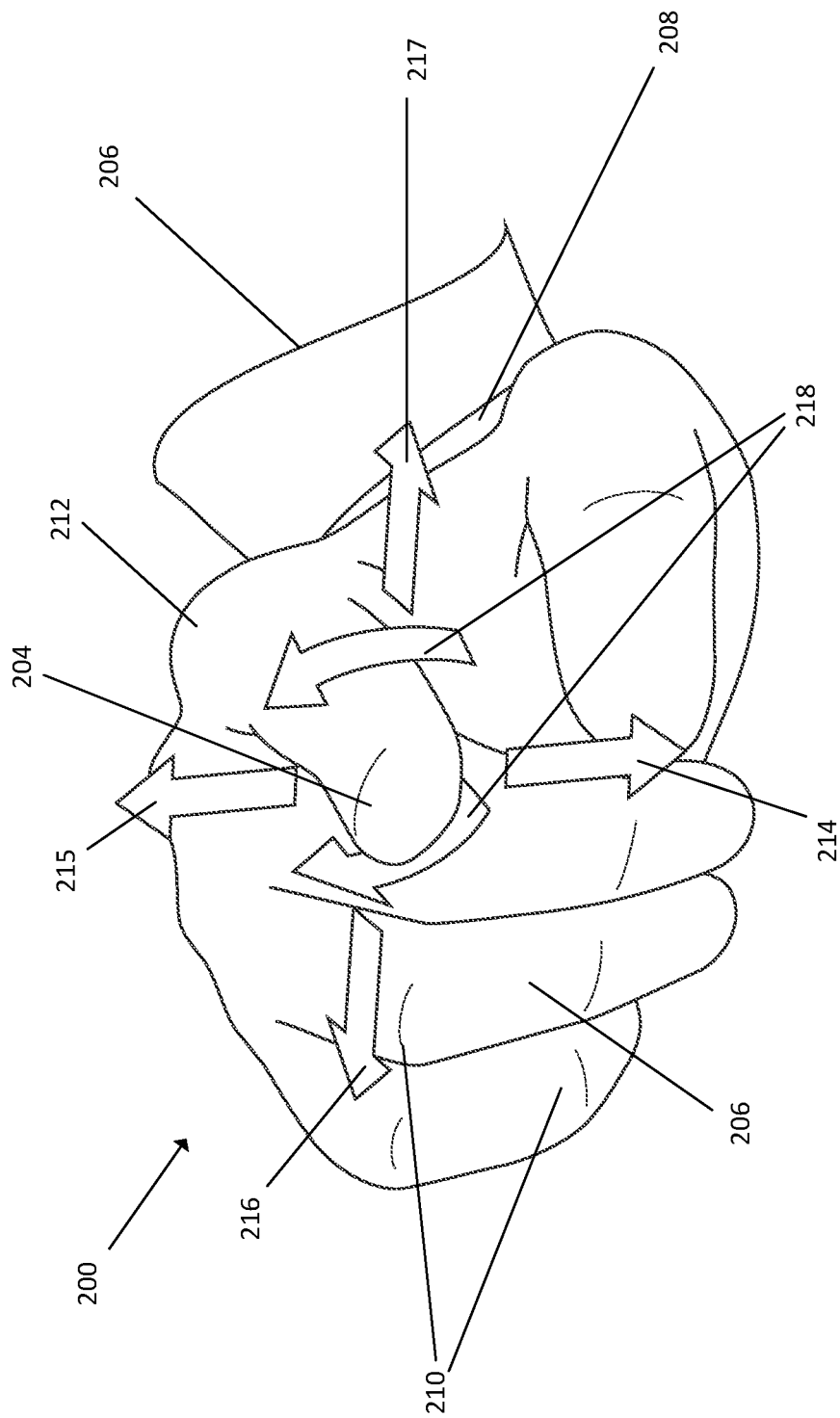
FIG. 4 is a perspective view of a patient's hand secured to a support, showing how the patient's finger may be moved by a user when secured to the jig of FIG. 1.

Referring to FIG. 4, a human finger 204 can move in several "degrees of freedom". Each joint type of the hand 200 has different degrees of freedom, according to available anatomical movements. An interphalangeal joint 210 has only one degree of freedom: flexion 214 and extension 215 (pitch). A metacarpophalangeal joint 212 is a saddle joint with two degrees of freedom: flexion 214 and extension 215, abduction 216 and adduction 217 (yaw). A wrist 208 has three degrees of freedom: abduction 216 and adduction 217, flexion 214 and extension 215, and rotation 218 (roll), although this is anatomically limited.

An optimal position of the fractured finger 204 may be obtained from any combination of one, or some, or all of the following movements: (i) flexion and extension; (ii) abduction and adduction; and (iii) rotation. Note that the rotational movement may be clockwise and counterclockwise about an axis that passes through the extended finger 204. Even though this is not a natural degree of freedom, it may be necessary to rotate the fractured finger 204 in such a manner for the clinician to reduce a fracture.

Figure 5:
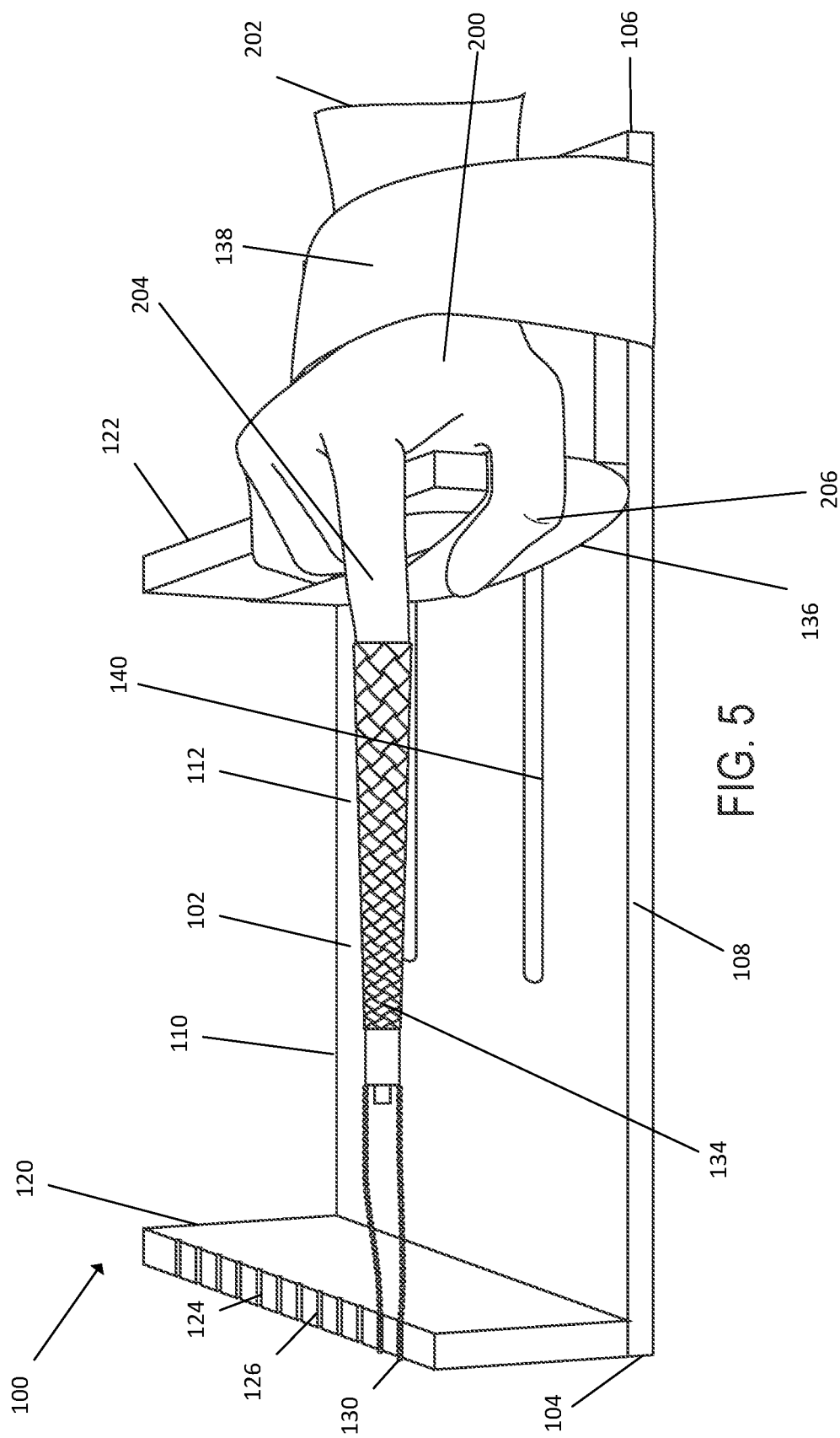
FIG. 5 is another perspective view of the jig of FIG. 1, showing a patient's hand and forearm secured to the jig.
Figure 6:
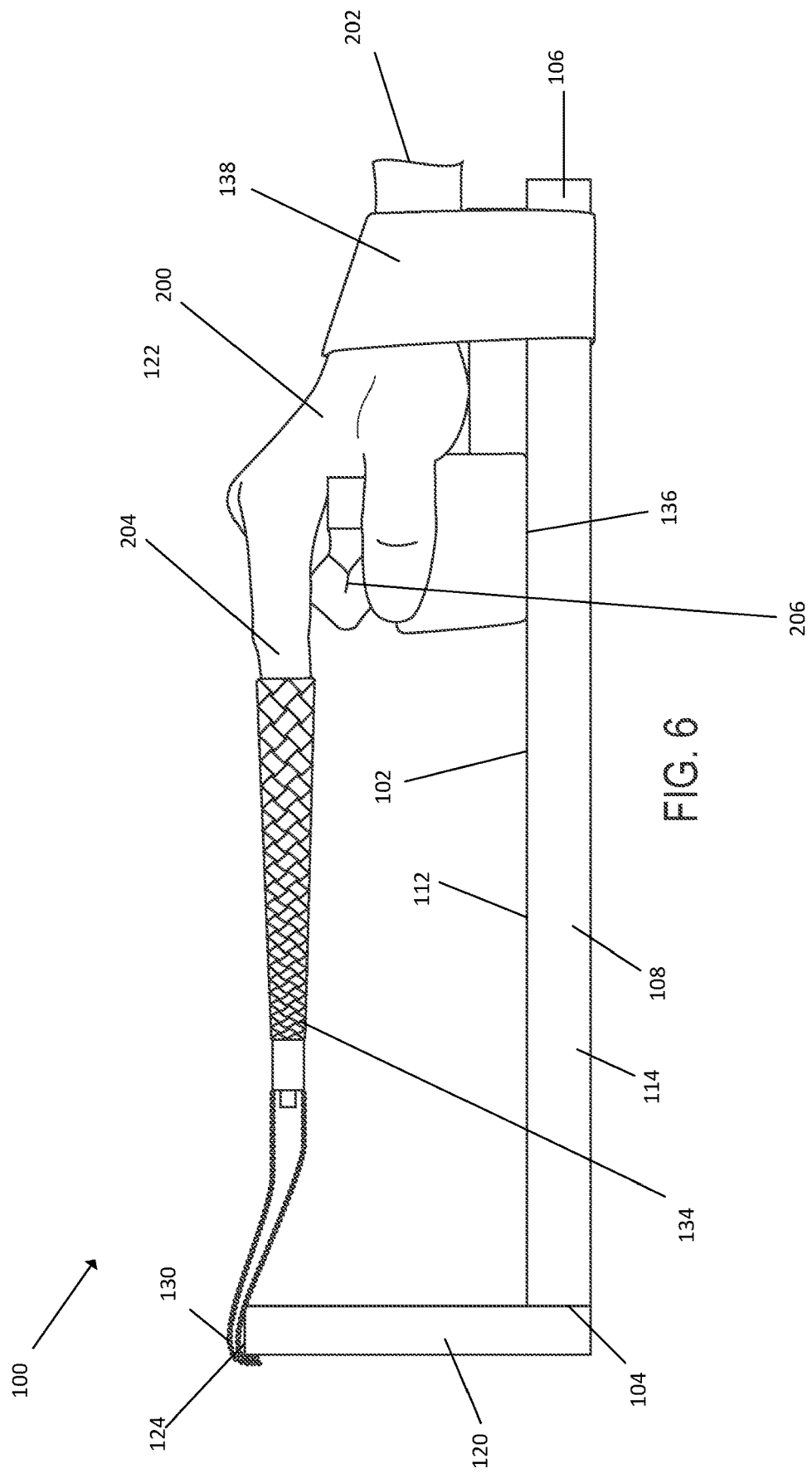
FIG. 6 is another side view of the jig of FIG. 1, showing a patient's hand and forearm secured to the jig.

Turning now to FIGS. 5-7, jig 100 is shown with a patient's hand 200 and forearm 202 secured in the jig. As shown, forearm strap 138 wraps around and secures a patient's forearm 202 to base 102. In certain embodiments, forearm strap 138 secures to itself by way of, but not limited to, snaps, hook and loop, or VELCRO®. Finger strap 136 secures the patient's fingers 206 that are not being repaired to second support 122. Like forearm strap 138, in certain embodiments, finger strap 136 secures to itself by way of, but not limited to, snaps, hook and loop, or VELCRO®.

In various embodiments, finger attachment 134 is secured to and positions a patient's fractured finger 204 in an optimal position for fracture reduction. In certain embodiments, finger attachment 134 tightens around the finger 204 when pulled, thereby providing even pressure to finger 204 while immobilizing the joints at the same time. In some embodiments, the relative positions of the hand 200, forearm 202, fractured finger 204, and other fingers 206 may adjust in relation to one another without departing from the principles of this disclosure.

Figure 8:
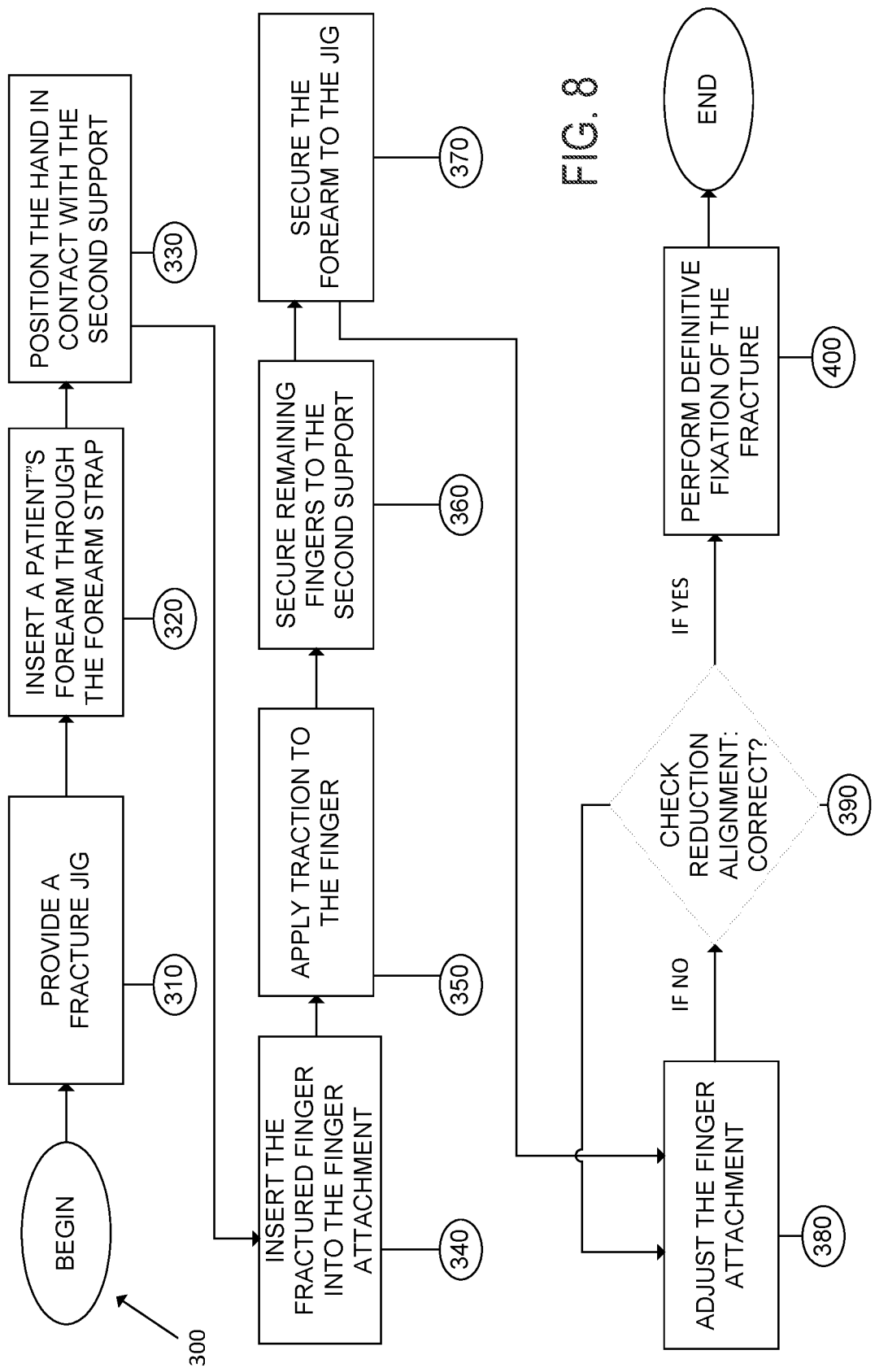
FIG. 8 is a flowchart of one embodiment of a surgical process in accordance with the principles of this disclosure.

Referring to FIG. 8, one exemplary method 300 for reducing a finger fracture 204 using jig 100 is shown. Once a patient has been prepped for surgery, a clinician inserts the hand 200 having a fractured finger through forearm strap 138 and rests the palm of the hand against second support 122. Next, the clinician secures fractured finger 204 to finger attachment 134 and applies traction to the fractured finger 204. Then the clinician and secures some or all of the remaining fingers 206 to second support 122 using finger strap 136.

Once the hand 200 is positioned and secured, the clinician secures a forearm 202 to jig 100 by tightening and securing forearm strap 138 and adjusts the alignment of the fractured finger 204 by adjusting the position of elongate members 130 along top edge 124 of first support 120. Once the elongate members 130 are in a desired position, the elongate members are secured to first support 120 (e.g., using optional notches 126). Adjusting the position of elongate members 130 aids in the overall alignment of the fracture by placing the fractured finger 204 in an optimal position for fracture reduction. Once the position of the fractured finger 204 is provisionally finalized, the clinician checks the fracture reduction and overall alignment. If needed, the clinician provisionally finalizes the position of the fractured finger by making additional adjustments to the position of the elongate members 130 and finger attachment 134. Once the position of the fractured finger 204 is finalized, a clinician performs a definitive fixation of the fracture. Although the method has been described in this order, the steps can be done in any suitable order without departing from the principles of this disclosure.

Figure 9:
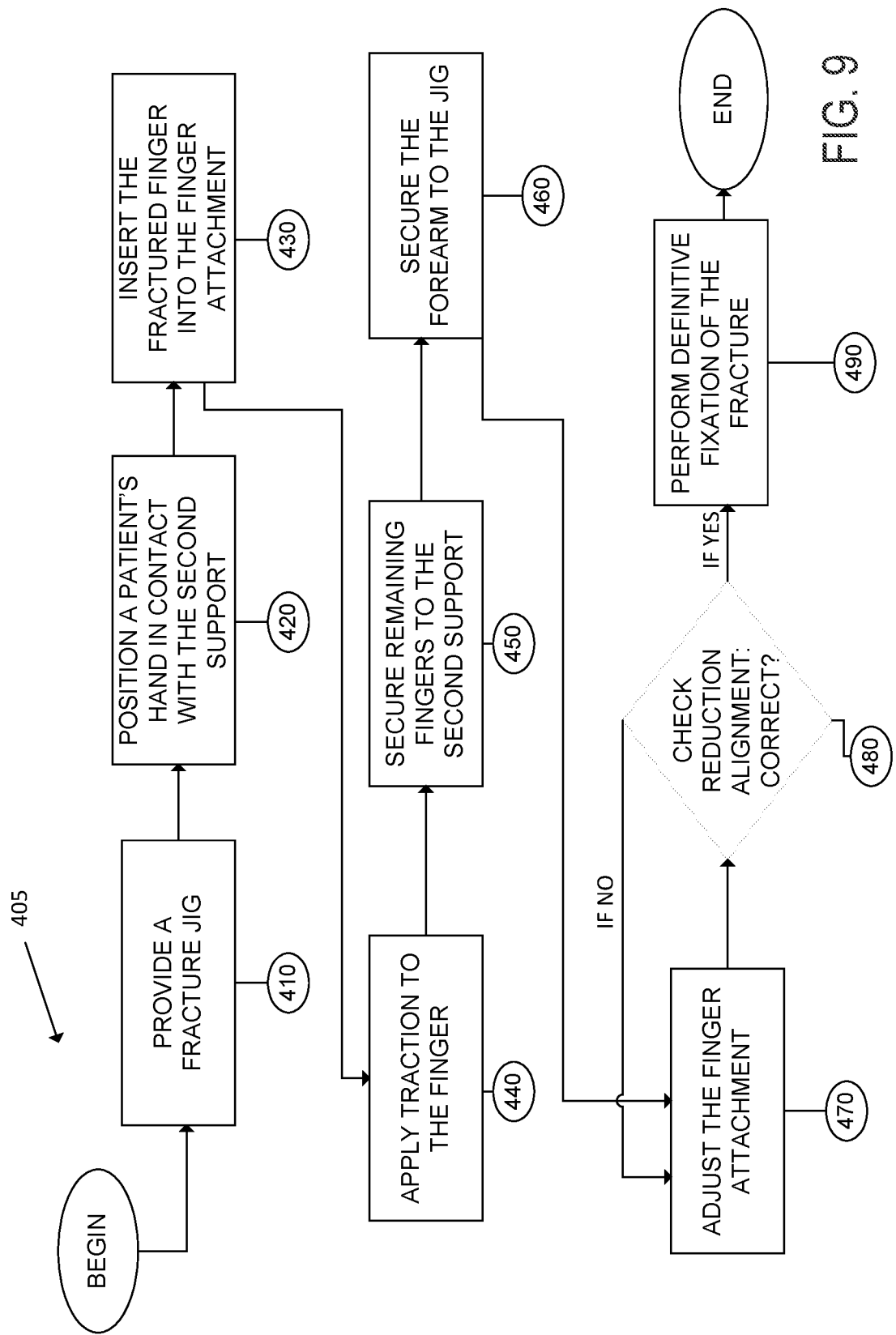
FIG. 9 is a flowchart of another embodiment of a surgical process in accordance with the principles of this disclosure.

Referring now to FIG. 9, another exemplary method 405 for reducing a finger fracture 204 using jig 100 is shown. Once a patient has been prepped for surgery, a clinician rests the palm of the hand against second support 122. Next, the clinician secures fractured finger 204 to finger attachment 134 and applies traction to the fractured finger 204. Then the clinician and secures some or all of the remaining fingers 206 to second support 122 using finger strap 136.

Once the hand 200 is positioned and secured, the clinician secures forearm 202 to jig 100 by tightening and securing forearm strap 138 and adjusts the alignment of the fractured finger 204 by adjusting the position of elongate members 130 along top edge 124 of first support 120. Once the elongate members 130 are in a desired position, the elongate members are secured to first support 120 using notches 126. Adjusting the position of elongate members 130 aids in the overall alignment of the fracture by placing the fractured finger 204 in an optimal position for fracture reduction. Once the position of the fractured finger 204 is provisionally finalized, the clinician checks the fracture reduction and overall alignment. If needed, the clinician may make additional adjustments to the position of the elongate members 130 and finger attachment 134. Once the position of the fractured finger 204 is finalized, a clinician performs a definitive fixation of the fracture. Although the method has been described in this order, the steps can be done in any suitable order without departing from the principles of this disclosure.

The embodiments were chosen and described in order to explain the principles of the devices and methods for using the same and their practical application so as to enable others skilled in the art to utilize the devices and methods for using the same and various embodiments and with various modifications as are suited to the particular use contemplated. Alternative embodiments will become apparent to those skilled in the art to which the present devices and methods for using the same pertain without departing from their spirit and scope. Accordingly, the scope of the present devices and methods for using the same is defined by the appended claims rather than the foregoing description and the exemplary embodiments described therein.

What is claimed is:

1. A jig for reducing a finger fracture comprising:
   a base having a first end and a second end;
   a first support positioned at the first end;
   a second support positioned between the first end and the second end;
   a finger attachment attached to the first support via a plurality of elongate members;
   a finger strap positioned between the second support and the first end, the finger strap selectively wrapping around the second support; and
   a forearm strap positioned between the second support and the second end, the forearm strap selectively wrapping around the base.

2. The jig of claim 1, wherein the second support is attached to the base.

3. The jig of claim 2, wherein the position of the second support is adjustable in relation to the first end and the second end.

4. The jig of claim 1, wherein the plurality of elongate members comprise a plurality of chains.

5. The jig of claim 1, wherein the plurality of elongate members comprise a plurality of wires.

6. The jig of claim 1, wherein the plurality of elongate members comprise a plurality of straps.

7. The jig of claim 1, wherein the plurality of elongate members comprise a first elongate member and a second elongate member.

8. The jig of claim 7, wherein:
the finger attachment selectively receives a finger; and
the first elongate member and the second elongate member are attached to the finger attachment in a coronal plane of the finger when the finger is received in the finger attachment.

9. The jig of claim 8, wherein the finger attachment, the first elongate member, and the second elongate member enable positioning of the finger in the coronal plane.

10. The jig of claim 9, wherein the finger attachment, the first elongate member, and the second elongate member provide rotational control of the finger.

11. The jig of claim 10, wherein changing the position of the first elongate member or the second elongate member adjusts the orientation of the finger attachment in relation to the second support.

12. The jig of claim 1, further comprising at least one guide tower positioned between the first support and the second support.

13. The jig of claim 12, wherein the guide tower comprises a k-wire guide.

* * * * *